US00PP31921P2

(12) United States Plant Patent
Kobayashi

(10) Patent No.: US PP31,921 P2
(45) Date of Patent: Jun. 30, 2020

(54) POINSETTIA PLANT NAMED 'PER1549'

(50) Latin Name: ***Euphorbia pulcherrima* Willd.**
Varietal Denomination: PER1549

(71) Applicant: DUMMEN GROUP B.V., De Lier (NL)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/501,410

(22) Filed: Apr. 9, 2019

(51) Int. Cl.
*A01H 5/02* (2018.01)
*A01H 6/38* (2018.01)

(52) U.S. Cl.
USPC ..... Plt./305

(58) Field of Classification Search
USPC ..... Plt./303, 305
See application file for complete search history.

*Primary Examiner* — Susan McCormick Ewoldt
(74) *Attorney, Agent, or Firm* — C. A. Whealy

(57) ABSTRACT

A new and distinct cultivar of Poinsettia plant named 'PER1549', characterized by its moderately compact, uniform, upright and mounded plant habit; moderately vigorous growth habit; freely and upright to somewhat outwardly branching habit; dark green-colored leaves; under natural season conditions, plants flower on or about November 25 in Southern California; large inflorescences with bright yellow to yellow orange-colored flower bracts; and good post-production longevity.

2 Drawing Sheets

Botanical designation: *Euphorbia pulcherrima* Willd.
Cultivar denomination: 'PER1549'.

BACKGROUND OF THE INVENTION

The present invention relates to a new and distinct cultivar of Poinsettia plant, botanically known as *Euphorbia pulcherrima* Willd., and hereinafter referred to by the cultivar name 'PER1549'.

The new Poinsettia plant is a product of a planned breeding program conducted by the Inventor in Encinitas, Calif. The objective of the breeding program is to create new uniform Poinsettia plants having large inflorescences with attractive flower bracts and excellent post-production longevity.

The new Poinsettia plant originated from a cross-pollination made by the Inventor in December, 2013 of a proprietary selection of *Euphorbia pulcherrima* Willd. identified as code number EZ09-000144-046, not patented, as the female, or seed, parent, with a proprietary selection of *Euphorbia pulcherrima* Willd. identified as code number EZ11-000125-043, not patented, as the male, or pollen, parent. The new Poinsettia plant was discovered and selected by the Inventor as a single flowering plant from within the progeny of the stated cross-pollination in a controlled greenhouse environment in Encinitas, Calif. in December, 2014.

Asexual reproduction of the new Poinsettia plant by terminal vegetative cuttings in a controlled greenhouse environment in Encinitas, Calif. since July, 2015 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'PER1549'. These characteristics in combination distinguish 'PER1549' as a new and distinct Poinsettia plant:

1. Moderately compact, uniform, upright and mounded plant habit.
2. Moderately vigorous growth habit.
3. Freely and upright to somewhat outwardly branching habit.
4. Dark green-colored leaves.
5. Under natural season conditions, plants flower on or about November 25 in Southern California.
6. Large inflorescences with bright yellow to yellow orange-colored flower bracts.
7. Good post-production longevity.

In side-by-side comparisons conducted in Encinitas, Calif., plants of the new Poinsettia differ primarily from plants of the female parent selection in flower bract color as plants of the new Poinsettia have bright yellow to yellow orange-colored flower bracts whereas plants of the female parent selection have light to golden yellow flower bracts with dark pink-colored flecks.

In side-by-side comparisons conducted in Encinitas, Calif., plants of the new Poinsettia differ primarily from plants of the male parent selection in the following characteristics:

1. Plants of the new Poinsettia are more compact than and not as vigorous as plants of the male parent selection.
2. Plants of the new Poinsettia have darker green-colored leaves than plants of the male parent selection.
3. Plants of the new Poinsettia have bright yellow to yellow orange-colored flower bracts whereas plants of the male parent selection have white to light yellow-colored flower bracts.

Plants of the new Poinsettia can be compared to plants of the *Euphorbia pulcherrima* Willd. 'PER975', disclosed in U.S. Plant Pat. No. 16,882. In side-by-side comparisons, plants of the new Poinsettia differ primarily from plants of 'PER975' in the following characteristics:

1. Plants of the new Poinsettia are more compact than and not as vigorous as plants of 'PER975'.
2. Plants of the new Poinsettia have darker green-colored leaves than plants of 'PER975'.
3. Plants of the new Poinsettia have bright yellow to yellow orange-colored flower bracts whereas plants of 'PER975' have pink to pale yellow-colored flower bracts.
4. Plants of the new Poinsettia flower about four days later than plants of 'PER975' when grown under natural season conditions in Southern California.

Plants of the new Poinsettia can also be compared to plants of the *Euphorbia pulcherrima* Willd. 'PER1409', disclosed in U.S. Plant Pat. No. 27,850. In side-by-side comparisons, plants of the new Poinsettia differ primarily from plants of 'PER1409' in the following characteristics:

1. Plants of the new Poinsettia are more compact than plants of 'PER1409'.
2. Plants of the new Poinsettia have bright yellow to yellow orange-colored flower bracts whereas plants of 'PER1409' have light yellow and peach-colored flower bracts with dark pink-colored flecks and spots.
3. Plants of the new Poinsettia flower about eight days later than plants of 'PER1409' when grown under natural season conditions in Southern California.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet is a side to top perspective view of a typical flowering plant of 'PER1549' grown in a 16.5-cm container.

The photograph on the second sheet is a close-up view of a typical flowering plant of 'PER1549' grown in a 16.5-cm container.

DETAILED BOTANICAL DESCRIPTION

Plants used in the aforementioned photographs and in the following detailed description were grown during the late autumn and early winter in 16.5-cm (plants used for the photographs and description) and 20-cm containers (plants used for the description only) in a polyethylene-covered greenhouse in Encinitas, Calif. under natural season conditions and cultural practices typical of commercial Poinsettia production. During the production of the plants, day temperatures averaged 26° C., night temperatures averaged 18° C. and light levels ranging from 4,500 to 5,000 foot-candles. Measurements and numerical values represent averages for typical flowering plants. A single plant was grown in the 16.5-cm containers and it was pinched one time. Four plants were grown in the 20-cm containers and they were not pinched. Plants were 23 weeks old when the photographs and the description were taken. In the following description, color references are made to The Royal Horticultural Society Colour Chart, 2017 Edition, except where general terms of ordinary dictionary significance are used.

Botanical classification: *Euphorbia pulcherrima* Willd. 'PER1549'.

Parentage:

*Female, or seed, parent.*—Proprietary selection of *Euphorbia pulcherrima* Willd. identified as code number EZ09-000144-046, not patented.

*Male, or pollen, parent.*—Proprietary selection of *Euphorbia pulcherrima* Willd. identified as code number EZ11-000125-043, not patented.

Propagation:

*Type.*—Terminal vegetative cuttings.

*Time to initiate roots.*—About seven to ten days at night temperatures about 20° C. and day temperatures about 27° C.

*Time to produce a rooted young plant.*—About four weeks at night temperatures about 20° C. and day temperatures about 27° C.

*Root description.*—Fibrous; typically white in color, actual color of the roots is dependent on substrate composition, water quality, fertilizer type and formulation, substrate temperature and physiological age of roots.

Plant description:

*Plant and growth habit.*—Moderately compact, uniform, upright and mounded plant habit; inverted triangle; large inflorescences with numerous flower bracts positioned above the foliar plane; moderately vigorous growth habit.

*Plant height.*—About 27 cm.

*Plant diameter or spread.*—About 45 cm.

*Lateral branch description.*—Quantity: Freely branching habit, about four to six lateral branches develop after pinching; upright branching habit. Length: About 18 cm. Diameter: About 6.5 mm. Internode length: About 1 cm to 1.5 cm. Strength: Strong. Aspect: About 30° to 45° from vertical. Texture: Smooth, glabrous. Luster: Moderately glossy. Color: Close to 143A.

*Leaf description.*—Arrangement: Alternate, simple. Length: About 8.5 cm. Width: About 6 cm. Shape: Ovate. Apex: Acuminate. Base: Obtuse with truncate tendencies. Margin: Mostly entire to slightly sinuate. Aspect: Outwardly to slightly upright; keeled. Texture, upper and lower surfaces: Rugose, glabrous; prominent venation on lower surface. Luster, upper surface: Slightly glossy. Luster, lower surface: Matte. Venation pattern: Pinnate, arcuate. Color: Developing and fully expanded leaves, upper surface: Darker green than N189A; venation, close to 146A to 146B. Developing and fully expanded leaves, lower surface: Close to 147A; venation, close to 146B to 146C. Leaf petioles: Length: About 3.5 cm to 4.2 cm. Diameter: About 3 mm. Texture, upper and lower surfaces: Smooth, glabrous. Luster, upper and lower surfaces: Moderately glossy. Color, upper and lower surfaces: Close to 146B to 146C.

Inflorescence description:

*Inflorescence type and habit.*—Terminal inflorescences are compound corymbs of cyathia with numerous colored flower bracts subtending the cyathia; inflorescences uniformly positioned above the foliar plane.

*Fragrance.*—None detected.

*Flowering response*.—Under natural season conditions, plants typically flower on or about November 25 in Southern California; under artificial long nyctoperiod/short photoperiod conditions, plants flower about eight weeks later.

*Post-production longevity*.—Good post-production longevity; plants of the new Poinsettia maintain good substance and flower bract color for about four to six weeks under interior conditions; flower bracts persistent and cyathia not persistent.

*Inflorescence diameter*.—About 26 cm.

*Inflorescence height* (*depth*).—About 4.5 cm.

*Flower bracts*.—Quantity per inflorescence: Numerous, about 33. Length, largest bracts: About 10 cm. Width, largest bracts: About 7.75 cm. Shape: Ovate. Apex: Acuminate. Base: Obtuse with truncate tendencies. Margin: Entire. Aspect: Mostly horizontal to slightly upright; keeled. Texture, upper and lower surfaces: Slightly rugose, glabrous; satiny. Luster, upper and lower surfaces: Matte. Venation pattern: Pinnate, arcuate. Color: Developing or transitional bracts, upper surface: Ground color, darker green than 147A; irregular and random sectors, close to 14A. Developing or transitional bracts, lower surface: Ground color, close to 144A and 146A; irregular and random sectors, close to 11A. Fully expanded bracts, upper surface: Close to 10A; color becoming closer to 17A with development. Fully expanded bracts, lower surface: Close to 10B; color becoming closer to 11A with development. Bract petioles: Length: About 4.5 cm. Diameter: About 2.5 mm. Texture, upper and lower surfaces: Smooth, glabrous. Luster, upper and lower surfaces: Moderately glossy. Color, upper and lower surfaces: Close to 154A.

*Cyathia*.—Quantity per corymb: About 16. Length: About 9 mm. Width: About 6 mm. Shape: Ovoid. Texture: Smooth, glabrous. Color, inner and outer surfaces: Close to 144A to 144B.

*Nectaries*.—Quantity per cyathium: One. Length: About 6 mm. Width: About 5 mm. Shape: Roughly elliptical. Texture: Smooth, glabrous. Color, inner and outer surfaces: Close to 17A.

*Peduncles*.—Length: About 5.5 mm. Diameter: About 2.5 mm. Strength: Strong. Aspect: Mostly upright to slightly outwardly. Texture: Smooth, glabrous. Color: Close to 144A to 144B.

*Reproductive organs*.—Stamens: Quantity per cyathium: About 12 to 15. Filament length: About 5 mm. Filament color: Close to 145C. Anther shape: Round to oval; bi-lobed. Anther length: Less than 1 mm. Anther color: Close to 12A. Amount of pollen: None observed. Pistils: Quantity per cyathium: One; triparted. Pistil length: About 7.5 mm. Stigma shape: Lanceolate, six-parted, recurved. Stigma color: Close to 6A. Style length: About 6 mm. Style color: Close to 144B to 144C. Ovary color: Close to 144B to 144C.

*Seeds and fruits*.—To date, seed and fruit production have not been observed on plants of the new Poinsettia.

Pathogen & pest resistance: To date, plants of the new Poinsettia have not been shown to be resistant to pathogens and pests common to Poinsettia plants.

Temperature tolerance: Plants of the new Poinsettia have been observed to tolerate temperatures ranging from about 16° C. to about 29° C.

It is claimed:

1. A new and distinct Poinsettia plant named 'PER1549' as illustrated and described.

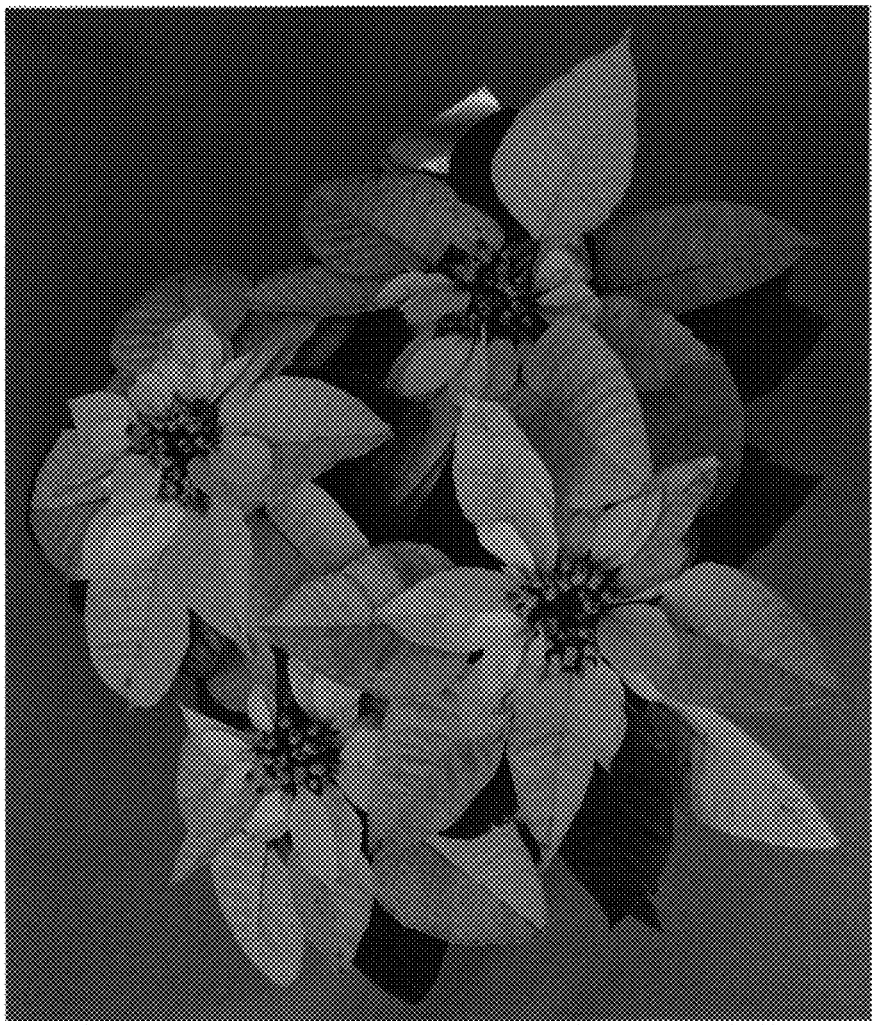

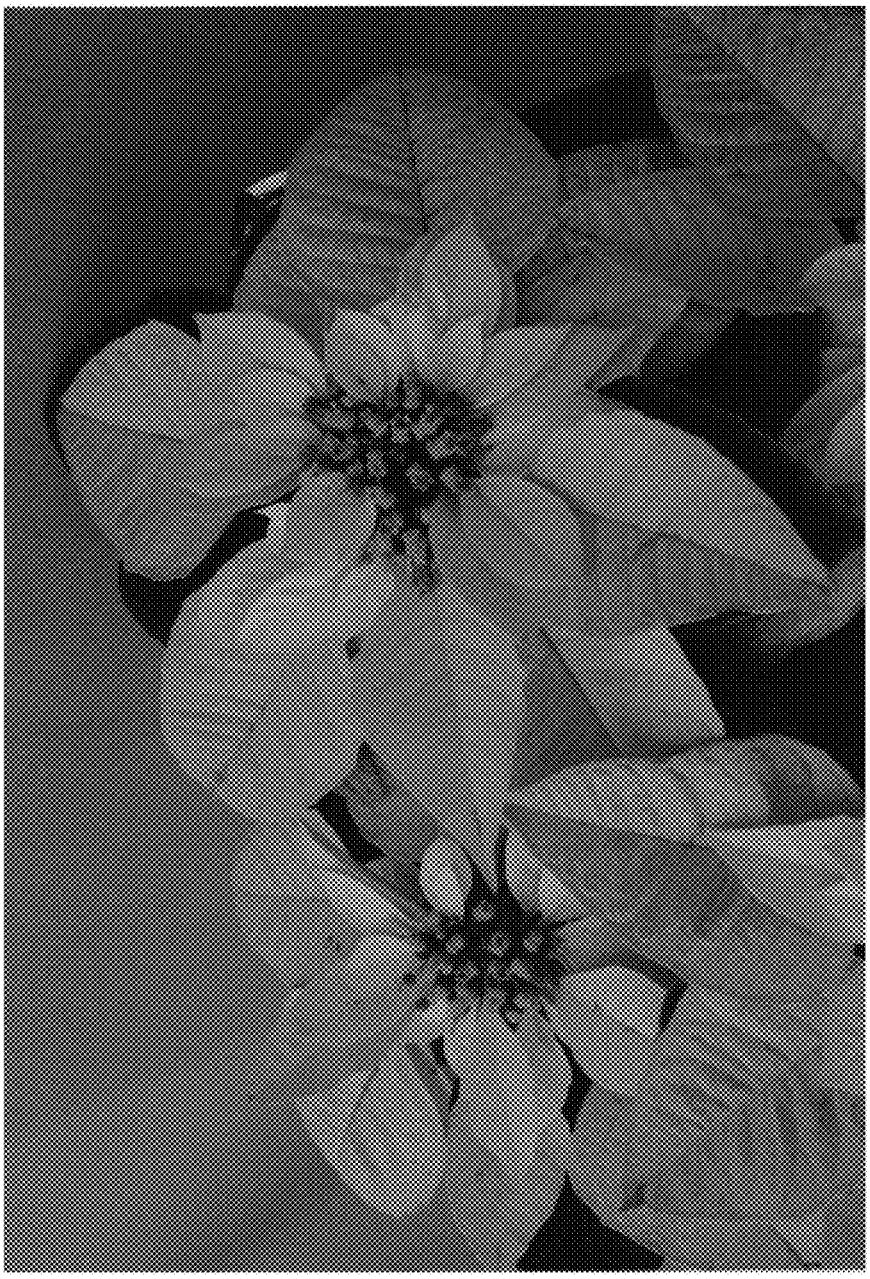

* * * * *